US010803987B2

(12) United States Patent
Bériault et al.

(10) Patent No.: US 10,803,987 B2
(45) Date of Patent: Oct. 13, 2020

(54) REAL-TIME MOTION MONITORING USING DEEP NEURAL NETWORK

(71) Applicant: Elekta, Inc., Atlanta, GA (US)

(72) Inventors: Silvain Bériault, Longueuil (CA); Martin Emile Lachaine, Montreal (CA)

(73) Assignee: Elekta, Inc., Atlanta, GA (US)

( * ) Notice: Subject to any disclaimer, the term of this patent is extended or adjusted under 35 U.S.C. 154(b) by 137 days.

(21) Appl. No.: 16/194,190

(22) Filed: Nov. 16, 2018

(65) Prior Publication Data

US 2020/0160972 A1  May 21, 2020

(51) Int. Cl.
| | |
|---|---|
| G16H 30/40 | (2018.01) |
| G06N 3/04 | (2006.01) |
| G06N 3/08 | (2006.01) |
| G16H 50/20 | (2018.01) |
| G06T 15/06 | (2011.01) |
| G06T 7/246 | (2017.01) |

(52) U.S. Cl.
CPC ........... *G16H 30/40* (2018.01); *G06N 3/0454* (2013.01); *G06N 3/08* (2013.01); *G06T 7/251* (2017.01); *G06T 15/06* (2013.01); *G16H 50/20* (2018.01); *G06T 2207/10081* (2013.01); *G06T 2207/10088* (2013.01); *G06T 2207/20081* (2013.01); *G06T 2207/20084* (2013.01)

(58) Field of Classification Search
CPC ...... G16H 30/40; G16H 50/20; G06N 3/0454; G06N 3/08; G06T 15/06; G06T 7/251; G06T 2207/20081; G06T 2207/10088; G06T 2207/20084; G06T 2207/10081
See application file for complete search history.

(56) References Cited

U.S. PATENT DOCUMENTS

| | | | |
|---|---|---|---|
| 9,495,746 | B2 | 11/2016 | Chou et al. |
| 9,764,162 | B1 | 9/2017 | Willcut et al. |
| 2014/0107390 | A1 | 4/2014 | Brown et al. |
| 2014/0213904 | A1 | 7/2014 | Chen et al. |
| 2016/0012592 | A1 | 1/2016 | Chou et al. |

(Continued)

FOREIGN PATENT DOCUMENTS

WO    WO-2011133606 A3    12/2011

OTHER PUBLICATIONS

A comparison of neural network approaches for on-line prediction in IGRT (Year: 2008).*

(Continued)

*Primary Examiner* — Nizar N Sivji
(74) *Attorney, Agent, or Firm* — Schwegman Lundberg & Woessner, P.A.; Sanjay Agrawal

(57) ABSTRACT

Systems and techniques may be used to estimate a relative motion of patient anatomy using a deep learning network during a radiotherapy treatment. For example, a method may include using a first deep neural network to relate input real-time partial patient measurements and a patient model including a reference volume to output patient states. The method may include using a second deep neural network to relate the patient states and the reference volume to relative motion information between the patient states and the reference volume. The deep neural networks may be used in real time to estimate a relative motion corresponding to an input image.

19 Claims, 11 Drawing Sheets

(56) References Cited

U.S. PATENT DOCUMENTS

| | | | |
|---|---|---|---|
| 2017/0330075 A1* | 11/2017 | Tuysuzoglu | G06N 3/0454 |
| 2017/0360325 A1 | 12/2017 | Hebert | |
| 2018/0075597 A1* | 3/2018 | Zhou | A61B 6/037 |
| 2018/0144466 A1* | 5/2018 | Hsieh | G06T 7/0012 |
| 2018/0182096 A1* | 6/2018 | Grady | G16H 50/50 |
| 2018/0310888 A1* | 11/2018 | Itu | G16H 50/20 |
| 2020/0058408 A1* | 2/2020 | Jain | G06N 3/04 |
| 2020/0065969 A1* | 2/2020 | Huang | G16H 50/50 |

OTHER PUBLICATIONS

Deep architecture neural network-based real-time image processing for image-guided radiotherapy (Year: 2017).*

Incorporating imaging information from deep neural network layers into image guided radiation therapy (IGRT) (Year: 2018).*

"International Application Serial No. PCT/US2019/058090, International Search Report dated Mar. 27, 2020", 7 pgs.

"International Application Serial No. PCT/US2019/058090, Invitation to Pay Additional Fees dated Feb. 6, 2020", 16 pgs.

"International Application Serial No. PCT/US2019/058090, Written Opinion dated Mar. 27, 2020", 13 pgs.

"International Application Serial No. PCT/US2019/061492, International Search Report dated Feb. 17, 2020", 4 pgs.

"International Application Serial No. PCT/US2019/061492, Written Opinion dated Feb. 17, 2020", 6 pgs.

Bjorn, Stemkens, et al., "Image-driven, model-based 3D abdominal motion estimation for MR-guided radiotherapy", Physics in Medicine and Biology, Institute of Physics Publishing, Bristol GB, vol. 61, No. 14, (Jun. 30, 2016), 21 pgs.

Chetvertkov, Mikhail A, et al., "Use of regularized principal component analysis to model anatomical changes during head and neck radiation therapy for treatment adaptation and response assessment", Medical Physics, Aip, Melville, NY, US, vol. 43, No. 10, (Sep. 6, 2016), XP012211772, ISSN: 0094-2405, DOI: 10.1118/1.4961746, [retrieved on Sep. 6, 2016], (Sep. 6, 2016), 5307-5319.

Foote, Markus D, et al., "Real-Time Patient-Specific Lung Radiotherapy Targeting using Deep Learning", Arxiv.Org, Cornell University Library, 201 Olin Library Cornell University Ithaca, NY 14853, (Jul. 23, 2018), XP081117672, (Jul. 23, 2018), 9 pgs.

Kontaxis, C, et al., "Towards fast onhne mtrafractson replanning for free-breathing stereotactic body radiation therapy with the MR-iinac", Physics in Medicine and Biology, Institute of Physics Publishing, Bristol GB, vol. 62, No. 18,, (Aug. 21, 2017), 16 pgs.

Li, Ruijiang, et al., "Real-time volumetric image reconstruction and 3D tumor localization based on a single x-ray projection image for lung cancer radiotherapy", Medical Physics, Aip, Melville, NY, US, vol. 37, No. 6, XP012135815, (May 21, 2010), 2822-2826.

Wei, Ran, et al., "A CNN based volumetric imaging method with single X-ray projection", 2017 IEEE International Conference On Imaging Systems And Techniques (IST), IEEE, XP033302050, DOI: 10.1109/IST.2017.8261550, [retrieved on Jan. 16, 2018], (Oct. 18, 2017), 1-6.

Chou, Chen-Rui, et al., "A learning-based patient repositioning method from limited-angle projections", (2010), 12 pgs.

Chou, Chen-Rui, et al., "CLARET:A Fast Deformable Registration Method Applied to Lung Radiation Therapy", Fourth International (MICCAI) Workshop on Pulmonary Image Analysis, (2011), 113-124.

Fischer, P, et al., "FlowNet: Learning Optical Flo with Convolutional Networks", CoRR, vol. abs/1504.06852, (2015), 9 pgs.

Jacobs, F, et al., "A Fast Algorithm to Calculate the Exact Radiological Path Through a Pixel Or Voxel Space", J Comput. Inf. Technol. vol. 6, (1998), 6 pgs.

Li, R, et al., "3D tumor localization through real-time volumetric x-ray imaging for lung cancer radiotherapy", Medical Physics, 38(5), (2011), 2783-2794.

Siddon, R L, "Fast calculation of the exact radiological path for a three-dimensional CT array", Med Phys vol. 12 No. 2, (Mar. 1985), 5 pgs.

Uzunova, H, et al., "Training CNNs for Image Registration from Few Sampleswith Model-based Data Augmentation", International Conference on Medical Image Computing and Computer-Assisted Intervention, (Sep. 4, 2017), 9 pgs.

Weinberger, Kilian Q, et al., "Metric Learning for Kernel Regression", Journal of Machine Learning Research, (2007), 8 pgs.

Xu, Y, et al., "A method for volumetric imaging in radiotherapy using single x-ray projection", Med Phys vol. 42 No. 5, (May 2015), 2498-2509.

* cited by examiner

REAL-TIME MOTION MONITORING USING DEEP NEURAL NETWORK

TECHNICAL FIELD

Embodiments of the present disclosure pertain generally to medical image and artificial intelligence processing techniques. In particular, the present disclosure pertains to use of a deep neural network for real-time motion monitoring.

BACKGROUND

In radiotherapy or radiosurgery, treatment planning is typically performed based on medical images of a patient and requires the delineation of target volumes and normal critical organs in the medical images. One challenge occurs with accurately tracking the various objects, such as a tumor, healthy tissue, or other aspects of patient anatomy when the patient is moving (e.g., breathing).

Current techniques are unable to directly measure a changing patient state in real-time. For example, some techniques use 2D imaging, such as 2D kV projections or 2D MRI slices, which are not able to completely track the various objects.

Other techniques may rely on detecting surface information, either directly or by tracking markers on a vest or a box affixed to the patient. These techniques assume that the surface information is correlated to internal patient state, which is often not accurate.

Yet other techniques may rely on implanting markers, such as magnetically tracked markers, or using x-ray detection of radio-opaque markers. These techniques are invasive and correspond only to limited points within the patient.

Regression models or other model-based techniques may be used to assist in motion monitoring. However, these techniques may be inaccurate or not able to track in real-time.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
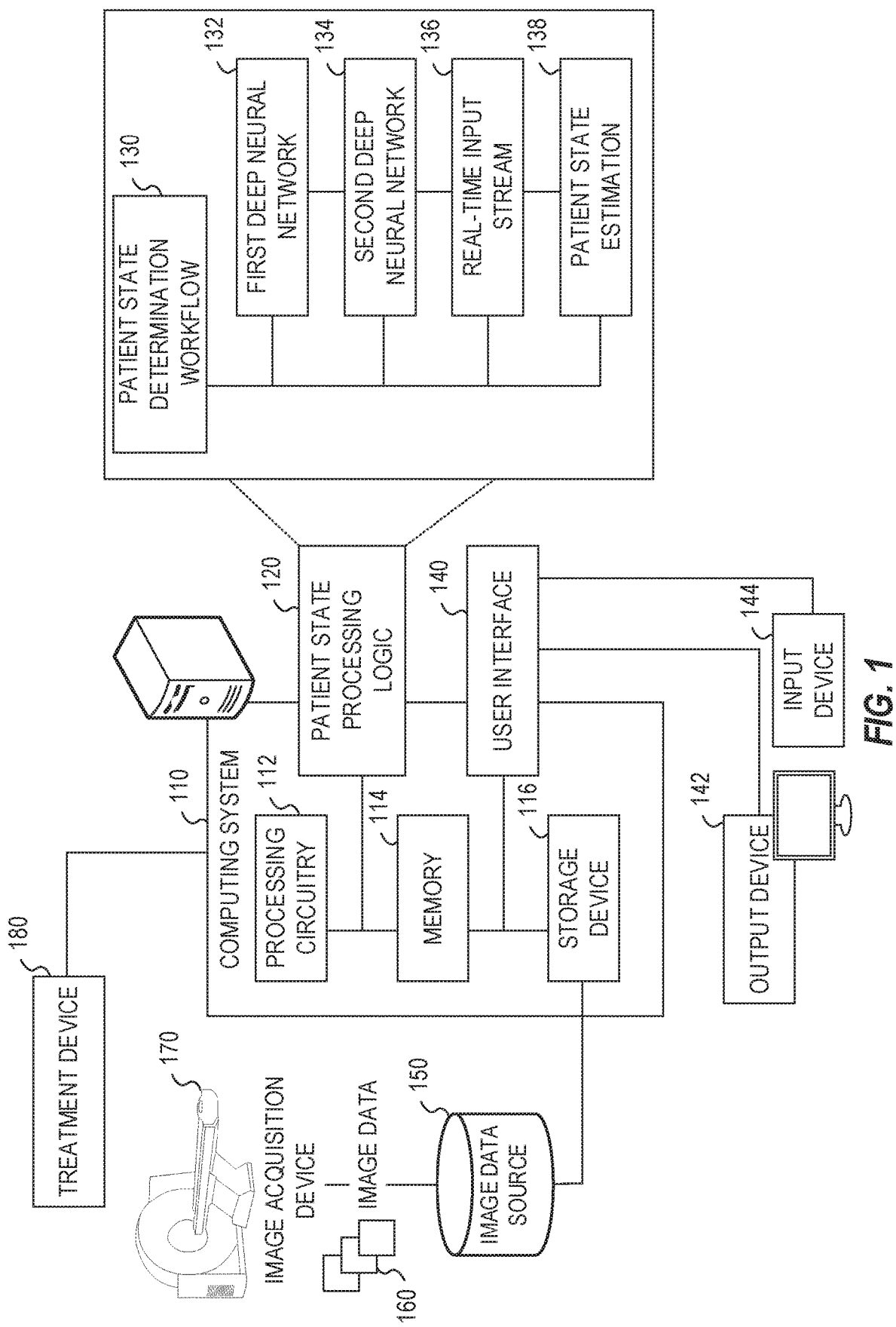
FIG. 1 illustrates an exemplary radiotherapy system adapted for performing image patient state estimation processing.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

Image guided radiation therapy (IGRT) is a technique that makes use of imaging of a patient, in treatment position, immediately prior to irradiation. This allows more accurate targeting of anatomy, such as an organs, tumors or organs-at-risk. If the patient is expected to move during treatment, for example motion caused by breathing which creates a quasi-periodic motion of a lung tumor, or bladder filling causing the prostate position to drift, additional margins may be placed around the target to encompass the expected patient motion. These larger margins come at the expense of high dose to surrounding normal tissue, which may lead to increased side-effects.

IGRT may use computed tomography (CT) imaging, cone beam CT (CBCT), magnetic resonance (MR) imaging, positron-emission tomography (PET) imaging, or the like to obtain a 3D or 4D image of a patient prior to irradiation. For example, a CBCT-enabled linac (linear accelerator) may consist of a kV source/detector affixed to the gantry at a 90 degree angle to a radiation beam, or a MR-Linac device may consist of a linac integrated directly with an MR scanner.

Localizing motion during the actual irradiation treatment delivery (intrafraction motion) may allow reduction of additional treatment margins that would otherwise be used to encompass motion, thus either allowing higher doses to be delivered, reduction of side-effects, or both. Many IGRT imaging technologies are generally not sufficiently fast for imaging intrafractional motion. For example, CBCT requires multiple kV images from various angles to reconstruct a full 3D patient image, and a 3D MR requires multiple 2D slices, or filling of the full 3D k-space, each which may take minutes to generate a full 3D image.

In some cases, the real-time or quasi-real-time data that would usually be completely acquired prior to generation of a 3D IGRT image, may be used as it is gathered to estimate the instantaneous 3D image at a much faster refresh rate from the incomplete, yet fast, stream of incoming information. For example, 2D kV projections or 2D MR slices may be used to estimate a full 3D CBCT-like or 3D MR-like image that evolves with the actual patient motion during treatment. Although fast, on their own these 2D images provide only a particular perspective of the patient, not the full 3D picture.

A patient state generator may receive partial measurements (e.g., a 2D image) as an input and generate (e.g., estimate) a patient state (e.g., a 3D image) as an output. To generate a patient state, the generator may use a first deep neural network. The output of the patient state generator may be further processed, for example by a second deep neural network to generate a deformation vector field (DVF) output. In an example, partial measurements used for input to the first deep neural network may be from a single modality, such as an x-ray projection or MRI slice, or from multiple modalities, such as positions of reflective surface markers on the patient's surface synchronized with x-ray projections.

Partial measurements may be received in a real-time stream of images (e.g., 2D images) taken from a kV imager or a MR imager, for example. The kV imager may produce stereoscopic 2D images for the real-time stream (e.g., two x-ray images that are orthogonal and acquired substantially simultaneously). The kV imager may be fixed in a room or coupled to a treatment device (e.g., attached to a gantry). The MR imager may produce 2D MR slices, which may be orthogonal or parallel. A patient state may be generated from an image or pair of images received. For example, at any given moment in time, the patient state for the last received image from the real-time stream may be generated.

In an example, a patient model may be based on data currently collected in a given fraction, in a pre-treatment phase (after the patient is set up and before the beam is turned on), from another fraction or during simulation/planning, using other patients, using generalized patient anatomy, using mechanical models, or any other information that may assist in defining a patient state from partial measurements. In an example, the patient model is a 4D dataset, acquired pre-treatment, which represents changes in patient state over a limited period of time (e.g. one representative respiratory cycle). The patient model may be used in a deep neural network to relate an input patient measurement (e.g., an image or pair of images from a real-time stream) to an output patient state.

The patient model in a 4D dataset may include the patient state that varies with a single parameter, such as phase in a respiratory cycle. The patient model may be used to build a time-varying patient state over a representative breathing cycle, which may treat each breath as more or less the same. This simplifies the modeling by allowing chunks of partial imaging data to be taken from different breathing cycles and assigned to a single representative breathing cycle. A 3D image may then be reconstructed for each phase 'bin'.

In an example, the patient state may be represented, for example, as a 3D image, or a 3D DVF plus a 3D reference image. These may be equivalent, since the elements of the 3D DVF and the 3D reference image may be used to obtain (e.g., deform the 3D reference image with the 3D DVF) the 3D image. An output of the systems and methods described herein may include a 3D DVF to deform an input 4D patient state model according to an input 2D image (e.g., from a real-time stream of images), to obtain a 3D image of the current patient state.

FIG. 1 illustrates an exemplary radiotherapy system adapted for using deep neural networks for real-time motion monitoring. The real-time motion monitoring may be used to determine a patient state to enable the radiotherapy system to provide radiation therapy to a patient based on specific aspects of captured medical imaging data. The radiotherapy system includes an image processing computing system 110 which hosts patient state processing logic 120. The image processing computing system 110 may be connected to a network (not shown), and such network may be connected to the Internet. For instance, a network can connect the image processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170, and a treatment device 180 (e.g., a radiation therapy device). As an example, the image processing computing system 110 can be configured to perform image patient state operations by executing instructions or data from the patient state processing logic 120, as part of operations to generate and customize radiation therapy treatment plans to be used by the treatment device 180.

The image processing computing system 110 may include processing circuitry 112, memory 114, a storage device 116, and other hardware and software-operable features such as a user interface 140, communication interface, and the like. The storage device 116 may store computer-executable instructions, such as an operating system, radiation therapy treatment plans (e.g., original treatment plans, adapted treatment plans, or the like), software programs (e.g., radiotherapy treatment plan software, artificial intelligence implementations such as deep learning models, machine learning models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 112 can execute sequences of computer program instructions, stored in memory 114, and accessed from the storage device 116, to perform various operations, processes, methods that will be explained in greater detail below.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a machine-readable medium on which is stored one or more sets of instructions and data structures (e.g., software) embodying or utilized by any one or more of the methodologies or functions described herein (including, in various examples, the patient state processing logic 120 and the user interface 140). The instructions may also reside, completely or at least partially, within the memory 114 and/or within the processing circuitry 112 during execution thereof by the image processing computing system 110, with the memory 114 and the processing circuitry 112 also constituting machine-readable media.

The memory device 114 or the storage device 116 may constitute a non-transitory computer-readable medium. For example, the memory device 114 or the storage device 116 may store or load instructions for one or more software applications on the computer-readable medium. Software applications stored or loaded with the memory device 114 or the storage device 116 may include, for example, an operating system for common computer systems as well as for software-controlled devices. The image processing computing system 110 may also operate a variety of software programs comprising software code for implementing the patient state processing logic 120 and the user interface 140. Further, the memory device 114 and the storage device 116 may store or load an entire software application, part of a software application, or code or data that is associated with a software application, which is executable by the processing circuitry 112. In a further example, the memory device 114 or the storage device 116 may store, load, or manipulate one or more radiation therapy treatment plans, imaging data, patient state data, dictionary entries, artificial intelligence model data, labels and mapping data, etc. It is contemplated that software programs may be stored not only on the storage device 116 and the memory 114 but also on a removable computer medium, such as a hard drive, a computer disk, a CD-ROM, a DVD, a HD, a Blu-Ray DVD, USB flash drive, a SD card, a memory stick, or any other suitable medium; such software programs may also be communicated or received over a network.

Although not depicted, the image processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the image processing computing system 110 may obtain image data 160 from the image data source 150, for hosting on the storage device 116 and the memory 114. In an example, the software programs operating on the image processing computing system 110 may convert medical images of one format (e.g., MRI) to another format (e.g., CT), such as by producing synthetic images, such as a pseudo-CT image. In another example, the software programs may register or associate a patient medical image (e.g., a CT image or an MR image) with that patient's dose distribution of radiotherapy treatment (e.g., also represented as an image) so that corresponding image voxels and dose voxels are appropriately associated. In yet another example, the software programs may substitute functions of the patient images such as signed distance functions or processed versions of the images that emphasize some aspect of the image information. Such functions might emphasize edges or differences in voxel textures, or other structural aspects. In another example, the software programs may visualize, hide, emphasize, or de-emphasize some aspect of anatomical features, patient measurements, patient state information, or dose or treatment information, within medical images. The storage device 116 and memory 114 may store and host data to perform these purposes, including the image data 160, patient data, and other data required to create and implement a radiation therapy treatment plan and associated patient state estimation operations.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 160 to be received or obtained in memory 114, and processed using the patient state processing logic 120. For example, the image processing computing system 110 may receive image data 160 from the image acquisition device 170 or image data sources 150 via a communication interface and network to be stored or cached in the storage device 116. The processing circuitry 112 may also send or update medical images stored in memory 114 or the storage device 116 via a communication interface to another database or data store (e.g., a medical facility database). In some examples, one or more of the systems may form a distributed computing/simulation environment that uses a network to collaboratively perform the embodiments described herein. In addition, such network may be connected to internet to communicate with servers and clients that reside remotely on the internet.

In further examples, the processing circuitry 112 may utilize software programs (e.g., a treatment planning software) along with the image data 160 and other patient data to create a radiation therapy treatment plan. In an example, the image data 160 may include 2D or 3D images, such as from a CT or MR. In addition, the processing circuitry 112 may utilize deep neural networks to generate an estimated patient state, for example a first deep neural network to receive an input partial measurement and a 4D patient model and output a patient state, and a second deep neural network to use the patient state and a reference image (e.g., a selected image or slice from the 4D patient model) to generate a DVF for deforming the 4D patient model based on the input partial measurement.

Further, such software programs may utilize patient state processing logic 120 to implement a patient state determination workflow 130, using the techniques further discussed herein. The processing circuitry 112 may subsequently then transmit the executable radiation therapy treatment plan via a communication interface and the network to the treatment device 180, where the radiation therapy plan will be used to treat a patient with radiation via the treatment device, consistent with results of the patient state determination workflow 130. Other outputs and uses of the software programs and the patient state determination workflow 130 may occur with use of the image processing computing system 110.

As discussed herein (e.g., with reference to the patient state determination discussed herein), the processing circuitry 112 may execute a software program that invokes the patient state processing logic 120 to implement functions including deep neural networks.

In an example, the image data 160 may include one or more MRI images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the image data 160 may also include or be associated with medical image processing data, for instance, training images, and ground truth images, contoured images, and dose images. In an example, the image data 160 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The image data 160 may be received and stored in any type of data or any type of format (e.g., in a Digital Imaging and Communications in Medicine (DICOM) format) that the image acquisition device 170 and the image processing computing system 110 may use to perform operations consistent with the disclosed embodiments.

In an example, the image acquisition device 170 may be integrated with the treatment device 180 as a single apparatus (e.g., a MRI device combined with a linear accelerator, also referred to as an "MR-linac", as shown and described in FIG. 3 below). Such an MR-linac can be used, for example, to precisely determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The image processing computing system 110 may communicate with an external database through a network to send/receive a plurality of various types of data related to image processing and radiotherapy operations. For example, an external database may include machine data that is information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The image processing computing system 110 can collect and obtain data, and communicate with other systems, via a network using one or more communication interfaces, which are communicatively coupled to the processing circuitry 112 and the memory 114. For instance, a communication interface may provide communication connections between the image processing computing system 110 and radiotherapy system components (e.g., permitting the exchange of data with external devices). For instance, the communication interface may in some examples have appropriate interfacing circuitry from an output device 142 or an input device 144 to connect to the user interface 140, which may be a hardware keyboard, a keypad, or a touch screen through which a user may input information into the radiotherapy system.

As an example, the output device 142 may include a display device which outputs a representation of the user interface 140 and one or more aspects, visualizations, or representations of the medical images. The output device 142 may include one or more display screens that display medical images, interface information, treatment planning parameters (e.g., contours, dosages, beam angles, labels, maps, etc.) treatment plans, a target, localizing a target or tracking a target, patient state estimations (e.g., a 3D image), or any related information to the user. The input device 144 connected to the user interface 140 may be a keyboard, a keypad, a touch screen or any type of device that a user may input information to the radiotherapy system. Alternatively, the output device 142, the input device 144, and features of the user interface 140 may be integrated into a single device such as a smartphone or tablet computer, e.g., Apple iPad®, Lenovo Thinkpad®, Samsung Galaxy®, etc.

Furthermore, any and all components of the radiotherapy system may be implemented as a virtual machine (e.g., via VMWare, Hyper-V. and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the image processing computing system 110, the image data sources 150, or like components, may be implemented as a virtual machine or within a cloud-based virtualization environment.

The patient state processing logic 120 or other software programs may cause the computing system to communicate with the image data sources 150 to read images into memory 114 and the storage device 116, or store images or associated data from the memory 114 or the storage device 116 to and from the image data sources 150. For example, the image data source 150 may be configured to store and provide a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) metadata, etc.) that the image data source 150 hosts, from image sets in image data 160 obtained from one or more patients via the image acquisition device 170. The image data source 150 or other databases may also store data to be used by the patient state processing logic 120 when executing a software program that performs patient state estimation operations, or when creating radiation therapy treatment plans. Further, various databases may store the data produced by the preliminary motion model (such as the dictionary), the correspondence motion model, or machine learning models, including the network parameters constituting the model learned by the network and the resulting predicted data. The image processing computing system 110 thus may obtain and/or receive the image data 160 (e.g., 2D MRI slice images, CT images, 2D Fluoroscopy images, X-ray images, 3D MRI images, 4D MRI images, etc.) from the image data source 150, the image acquisition device 170, the treatment device 180 (e.g., a MRI-Linac), or other information systems, in connection with performing image patient state estimation as part of treatment or diagnostic operations.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 170 in "real-time" while a patient is undergoing radiation therapy treatment, for example, when using the treatment device 180 (with "real-time" meaning acquiring the data in 10 milliseconds or less). In another example for some applications, real-time may include a timeframe within (e.g., up to) 200 or 300 milliseconds. In an example, real-time may include a time period fast enough for a clinical problem being solved by techniques described herein. In this example, real-time may vary depending on target speed, radiotherapy margins, lag, response time of a treatment device, etc.

The patient state processing logic 120 in the image processing computing system 110 is depicted as implementing a patient state determination workflow 130 with various deep neural networks and estimation of a patient state (e.g., a DVF). In an example, the patient state determination workflow 130 operated by the patient state processing logic 120 uses a first deep neural network 132 trained to output a patient state based on an input of a partial measurement (e.g., real-time 2D image) and a 4D patient model with a reference image. The patient state determination workflow 130 includes a second deep neural network 134 trained to output a DVF based on an input of the patient state and the reference image from the first deep neural network 132. The patient state determination workflow 130 includes receiving a real-time input stream 136 (e.g., 2D partial measurements, such as from a CT or MR). An image from the real-time input stream 136 may be fed into the trained first and second deep neural networks 132 and 134 to generate a DVF relating the image to the 4D model. The patient state determination workflow 130 includes estimating a patient state 138 using the trained first and second deep neural networks 132 and 134 and a current patient measurement (e.g., 2D image) from the real-time input stream 136, the patient state 138 being represented in an example by the DVF.

Figure 2:
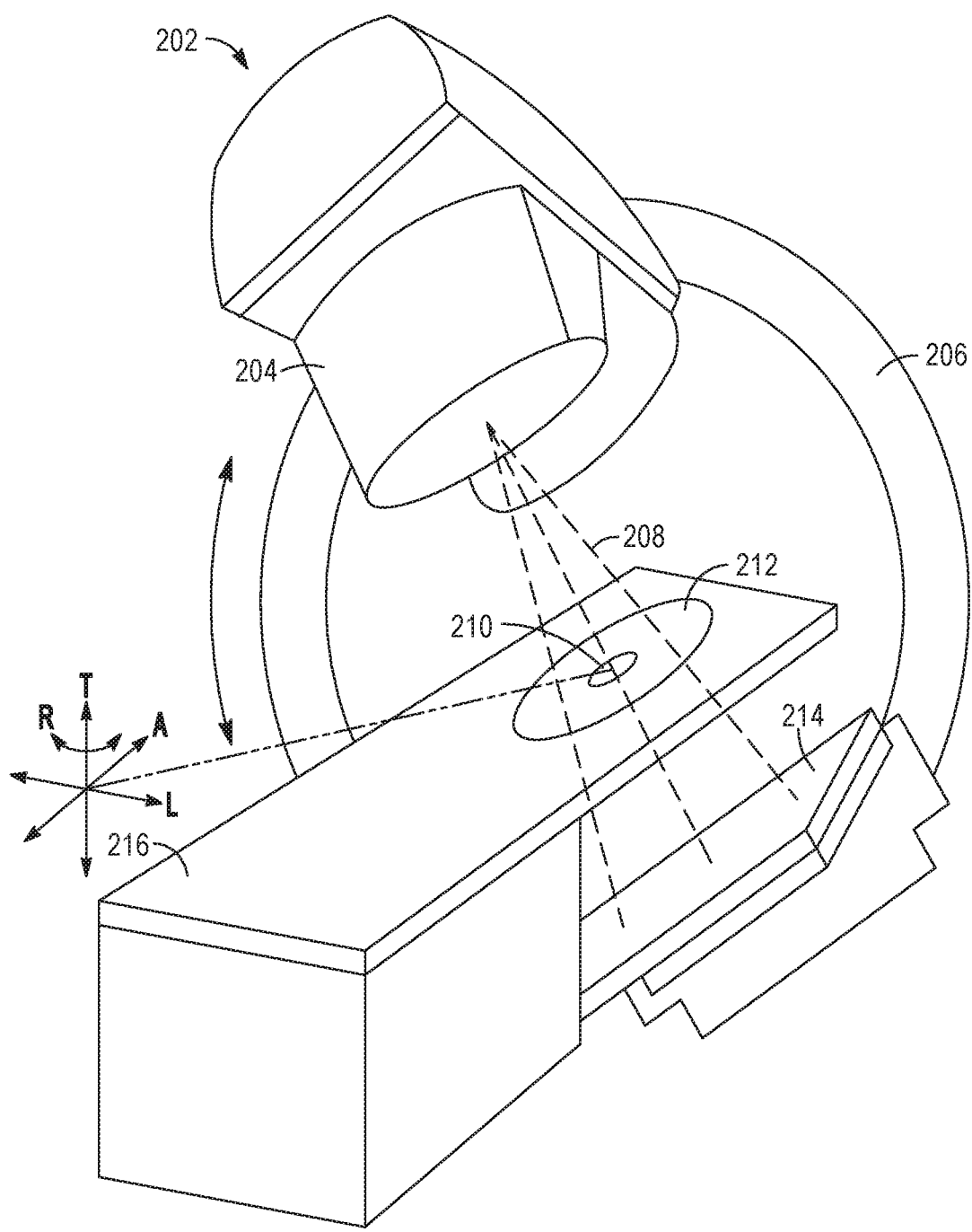
FIG. 2 illustrates an exemplary image-guided radiotherapy device.

FIG. 2 illustrates an exemplary image-guided radiotherapy device 202, that includes include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC).

As an example, a patient may be positioned in a region 212, supported by the treatment couch 216 to receive a radiation therapy dose according to a radiation therapy treatment plan (e.g., a treatment plan generated by the radiotherapy system of FIG. 1). The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an example, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within the radiotherapy system or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, an MR-linac, or radiotherapy portal imaging device, etc., as would be recognized by one of ordinary skill in the art.

Figure 3:
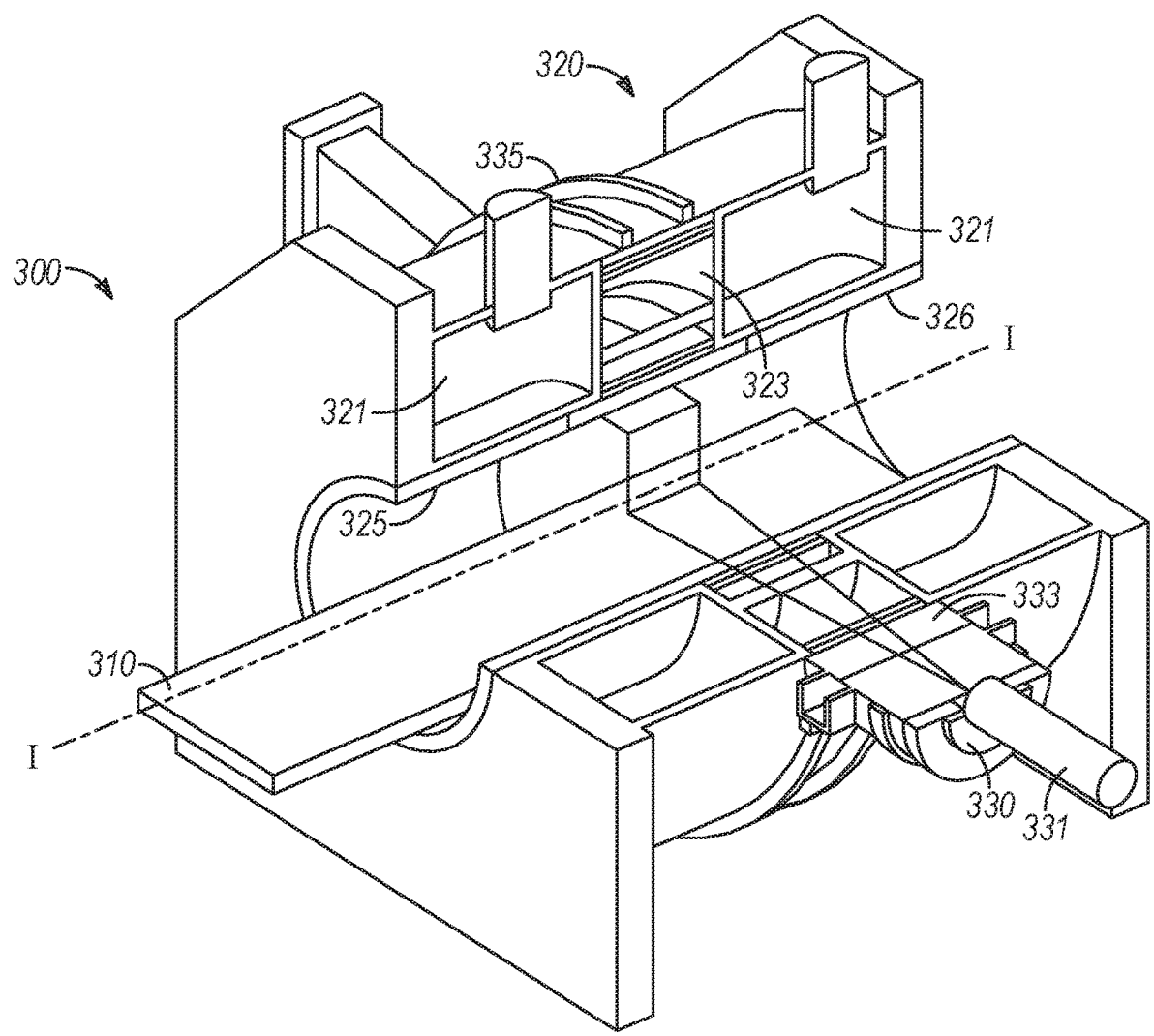
FIG. 3 illustrates a partially cut-away view of an exemplary system including a combined radiation therapy system and an imaging system, such as a nuclear magnetic resonance (MR) imaging system.

FIG. 3 depicts an exemplary radiation therapy system 300 (e.g., known in the art as a MR-Linac) that can include combining a radiation therapy device 202 and an imaging system, such as a nuclear magnetic resonance (MR) imaging system consistent with the disclosed embodiments. As shown, system 300 may include a couch 310, an image acquisition device 320, and a radiation delivery device 330. System 300 delivers radiation therapy to a patient in accordance with a radiotherapy treatment plan. In some embodiments, image acquisition device 320 may correspond to image acquisition device 170 in FIG. 1 that may acquire images.

Couch 310 may support a patient (not shown) during a treatment session. In some implementations, couch 310 may move along a horizontal, translation axis (labelled "I"), such that couch 310 may move the patient resting on couch 310 into or out of system 300. Couch 310 may also rotate around a central vertical axis of rotation, transverse to the translation axis. To allow such movement or rotation, couch 310 may have motors (not shown) enabling the couch to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321, and may be displaced along that central axis. The displacement may create a gap, or window, between coils 325 and 326. In the embodiments where magnet 321 also includes a central window 323 between coils, the two windows may be aligned with each other.

Image acquisition is used to track tumor movement. At times, internal or external surrogates may be used. However, implanted seeds may move from their initial positions or become dislodged during radiation therapy treatment. Also, using surrogates assumes there is a correlation between tumor motion and the displacement of the external surrogate. However, there may be phase shifts between external surrogates and tumor motion, and their positions may frequently lose correlation over time. It is known that there may be mismatches between tumor and surrogates upward of 9 mm. Further, any deformation of the shape of a tumor is unknown during tracking.

An advantage of magnetic resonance imaging (MRI) is in the superior soft tissue contrast that is provided to visualize the tumor in more detail. Using a plurality of intrafractional MR images allows the determination of both shape and position (e.g., centroid) of a tumor. In addition, MRI images improve any manual contouring performed by, for example, a radiation oncologist, even when auto-contouring software (e.g., ABAS®) is utilized. This is because of the high contrast between the tumor target and the background region provided by MR images.

Another advantage of using an MR-Linac system is that a treatment beam can be continuously on and thereby executing intrafractional tracking of the target tumor. For instance, optical tracking devices or stereoscopic x-ray fluoroscopy systems can detect tumor position at 30 Hz by using tumor surrogates. With MRI, the imaging acquisition rates are faster (e.g., 3-6 fps). Therefore, the centroid position of the target may be determined, artificial intelligence (e.g., neural network) software can predict a future target position. An added advantage of intrafractional tracking by using an MR-Linac is that the by being able to predict a future target location, the leaves of the multi-leaf collimator (MLC) will be able to conform to the target contour a its predicted future position. Thus, predicting future tumor position using MRI occurs at the same rate as imaging frequency during tracking. By being able to track the movement of a target tumor clearly using detailed MRI imaging allows for the delivery of a highly conformal radiation dose to the moving target.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, or radiotherapy portal imaging device, etc. As would be recognized by one of ordinary skill in the art, the above description of image acquisition device 320 concerns certain embodiments and is not intended to be limiting.

Radiotherapy device 330 may include the source of radiation 331, such as an X-ray source or a linear accelerator, and a multi-leaf collimator (MLC) 333. Radiotherapy device 330 may be mounted on a chassis 335. One or more chassis motors (not shown) may rotate chassis 335 around couch 310 when couch 310 is inserted into the treatment area. In an embodiment, chassis 335 may be continuously rotatable around couch 310, when couch 310 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 310, image acquisition device 320, and radiotherapy device 330. The control circuitry of radiotherapy device 330 may be integrated within system 300 or remote from it.

During a radiotherapy treatment session, a patient may be positioned on couch 310. System 300 may then move couch 310 into the treatment area defined by magnetic coils 321, 325, 326, and chassis 335. Control circuitry may then control radiation source 331, MLC 333, and the chassis motor(s) to deliver radiation to the patient through the window between coils 325 and 326 according to a radiotherapy treatment plan.

Figure 4:
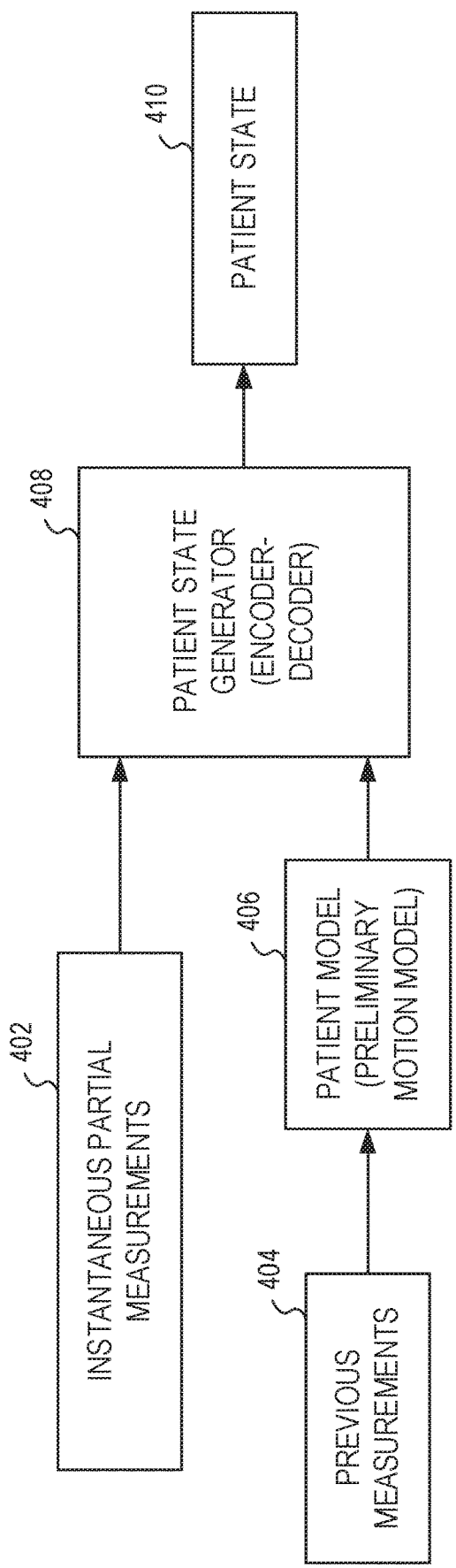
FIG. 4 illustrates an exemplary flow diagram for estimating a patient state using partial measurements and a preliminary patient model.

FIG. 4 illustrates an exemplary flow diagram for estimating a patient state. FIG. 4 includes a patient state generator 408 for estimating a patient state using an encoder-decoder convolutional neural network (CNN) or other neural network. The patient state generator 408 uses an instantaneous partial measurement 402 and a preliminary motion model of a patient 406 to estimate a patient state, output at block 410. The preliminary motion model 406 is generated using previous measurements 404, including previous patient states corresponding to the previous measurements 404.

In practical radiotherapy applications, partial measurements (e.g., a 2D image or image slice) provide incomplete information about the patient state (e.g., a 3D image). For example, a 2D MRI slice is a single cut through a 3D representation of the patient, and an x-ray projection is an integration through voxels along ray-lines of a 3D representation. Using either image results in impartial information (e.g., a 2D image rather than a 3D representation of patient anatomy). The patient state generator 408 may use the partial information and the patient model 406 generated from past measurements and/or offline (pre-treatment) acquisitions to estimate the patient state 410. The patient model generator 408 may include creation of a low dimensional patient state representation.

4D images may include a series of 3D images of a representative respiratory cycle. For example, for a 4D CBCT, a number of x-ray projections are acquired and sorted into a number of bins. Sorting may be done, for example, by detecting a diaphragm position in each projection directly in the images, or using a separate respiratory signal acquired simultaneously with the kV projections, and binning the projection according to the phase or amplitude of the signal. Each bin is then reconstructed separately with the kV projections assigned to that bin to form a 3D image per bin. Similar techniques may be used to generate a 4D MR image. A model may then be constructed using the 4D image as an interim step. In some cases the interim step of reconstructing a 4D image may not be necessary, and the low dimensional state representation may be created directly from the measurements.

A DVF-based motion model (output as the patient state 410, for example) provides a mechanism for deforming a reference patient state (e.g., treatment information as defined on a 3D reference image) to the specific anatomy exhibited in each of the other phases of the representative respiratory cycle represented in the 4D dataset.

The systems and methods described herein include a deep learning framework for mapping instantaneous partial measurements (e.g., 2D images) to their underlying complete 3D patient states (e.g., output estimates). In an example, this 2D to 3D problem may be reformulated into a (2D+4D) to 3D problem.

Machine learning techniques may be used to learn 2D to 3D inferences between instantaneous partial measurements (2D) and their underlying 3D patient state. In such examples, a 4D dataset may be used to generate training pairs (2D measurement, 3D patient states). However, these techniques may be limited by temporal relationships that exist between consecutive patient states that are not considered. Other limitations may include the need to retrain the patient state generator for each individual patient (e.g., using the patient's own patient model). Lengthy training time may significantly impact the treatment workflow, especially if the 4D patient model is acquired just before the radiotherapy treatment. Another limitation may include training the model offline using a large population of 4D patient models, which would lack sufficient patient-specificity of the purpose of motion management.

The systems and methods described herein may solve these problems and limitations by training two (or more) deep neural networks to learn dependencies between features found in 2D partial measurements and features found in a 4D spatio-temporal patient model. The output of the two or more deep neural networks may include an estimate of the underlying patient state for unseen pairs of input measurements/models. These systems and techniques may include a patient state generator that exploits both spatial and temporal dependencies in the data. Furthermore, the patient state generator may be trained only once using a large database of multi-patient data, while remaining patient-specific, since the patient's own model is fed as input to the network.

In an example, the systems and methods described herein may be suitable for tracking both the tumor and other surrounding organs without any need for invasively implanted markers.

In an example, the systems and methods described herein may not require computationally expensive deformable image registration (DIR) on the 4D patient model. In this example, there may be no pre-treatment delays, and thus no impact on the treatment workflow. Furthermore, the systems and methods described herein are not limited to accuracy of the displacement vector fields (DVF) produced by way of DIR.

The systems and methods described herein may be model-free (other than input patient models, which are data driven) and solely driven by the training data. As such, the systems and methods described herein may be less subject to under-fitting than a model-based method, which may include a strong linearity assumption.

A neural network is trained with a large number of patient models and may be generalized to changes or drifts in the motion that may occur during the treatment. In an example, compared to models trained using a single (time-constrained) patient model (one average respiratory cycle), the systems and methods described herein may be more generalized. Once trained, the neural network may adapt to inter-fraction change in tumor size and changes in motion of surrounding organs without any lengthy re-training, for example, by injecting a different (e.g., updated) input patient model.

Figure 5:
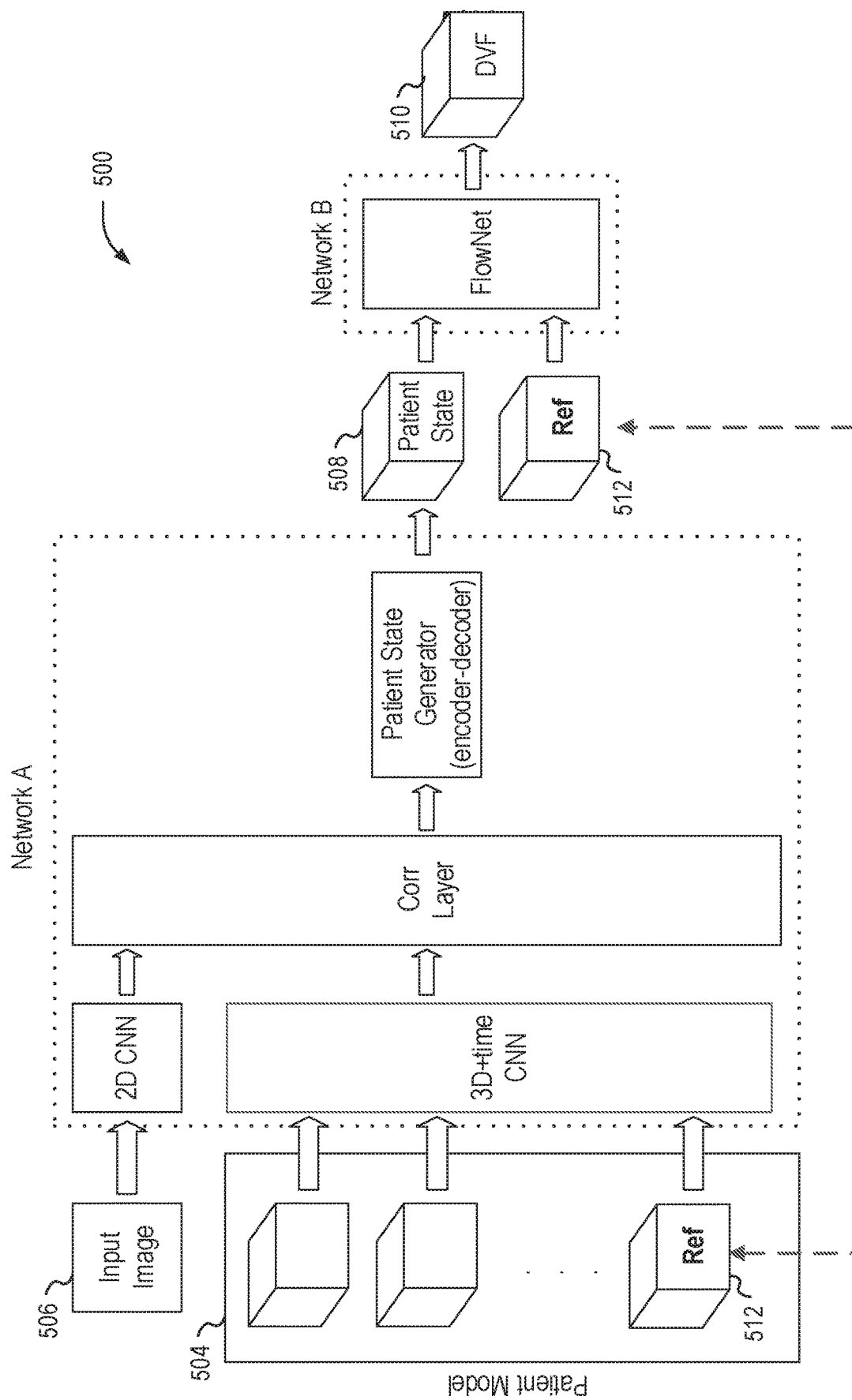
FIG. 5 illustrates an exemplary deep neural network architecture overview block diagram.

FIG. 5 illustrates an exemplary deep neural network architecture 500 overview block diagram. The deep neural network architecture 500 includes two parts. A first part, labeled in FIG. 5 as "Network A" may be used to interpolate an input 4D patient model 504 in a temporal dimension, with input 2D partial measurement 506 as a cue, to produce a raw 3D patient state estimate 508. A second part, labeled in FIG. 5 as "Network B" computes the relative motion, output as a 3D displacement vector field (DVF) 510 between the raw 3D patient state 508 and a reference volume 512 on which the treatment plan was defined (e.g. higher-level information about organs at risk, GTV, etc.). In an example, the reference volume 512 is one phase of the 4D patient model 504 (e.g., one phase is selected to be the reference volume 512 before the 4D patient model 504 is input to Network A. In other examples, the reference volume 512 may be a separately acquired dataset.

In an example, Network A is used to generate a raw 3D patient state 508 based on an input 4D patient model (acquired pre-treatment) and a current, real-time 2D image measurement 506 of a patient. Network B may be used to compute a relative motion between the generated 3D patient state 508 and a reference volume 512, onto which the treatment plan was defined. The output DVF 510 maybe generated in real-time from the input image 506.

Additional details regarding the functioning and output of Network A are included below with respect to FIGS. 6A-6B.

In an example, Network B computes a relative motion between the raw patient state 508 (output of Network A) and a reference volume 512 (e.g., a phase at an end-of-exhale of a patient) in the patient model on which a higher-level clinical treatment plan was defined (e.g., definitions of GTV, organs at risk, etc.). In an example, a 3D extension to 2D FlowNet architecture may be used to estimate a displacement vector field (DVF) 510 between the interpolated 3D patient state 508 (from Network A) and the 3D reference volume 512. This DVF 510 may be used to adapt the treatment plan to changes detected between the reference volume 512 (on which the treatment plan was made) and the most up-to-date patient state 508. In another example, a conventional deformable image registration (DIR) technique may be used. In an example, a deep neural network architecture is non-iterative and may be more suitable for live motion monitoring.

The two-network architecture 500 is used instead of a single deep neural network to improve the ultimate output. An end-to-end network may not be possible. Instead, by using two networks, the reference volume 512 may be used as an input to both networks to create a realistic, ground-truth, training input including 2D measurement 506 and 4D patient model 504 to output the DVF 510. The patient model interpolation (Network A) followed by relative motion estimation (Network B) may be more accurate than an end-to-end network. Further, the two-network architecture 500 may significantly reduce training complexity and increase feasibility, for example, with regards to generating ground-truth training samples.

Figure 6A:
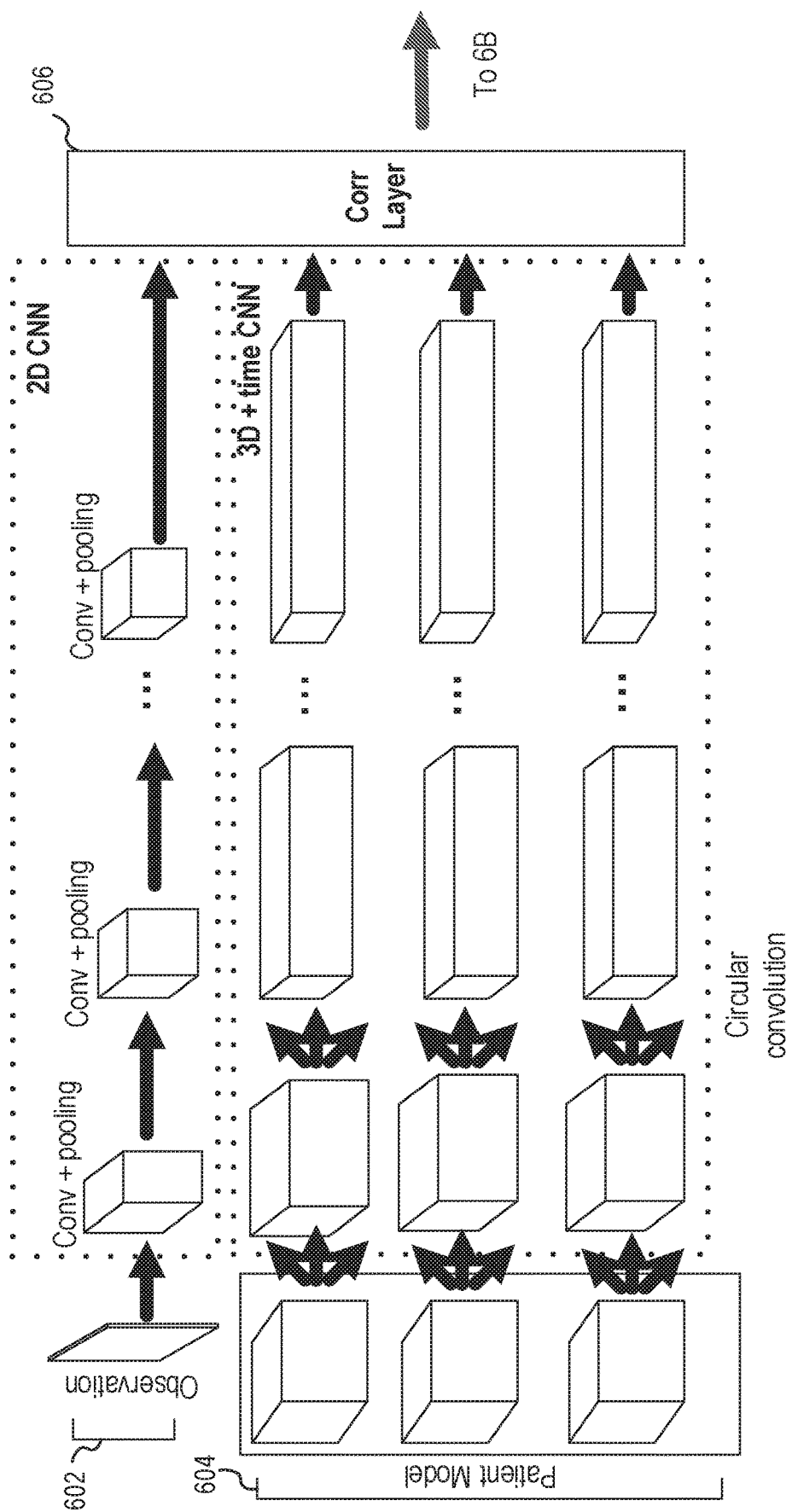
FIGS. 6A-6B illustrate exemplary detailed deep neural network architecture block diagrams.
Figure 6B:
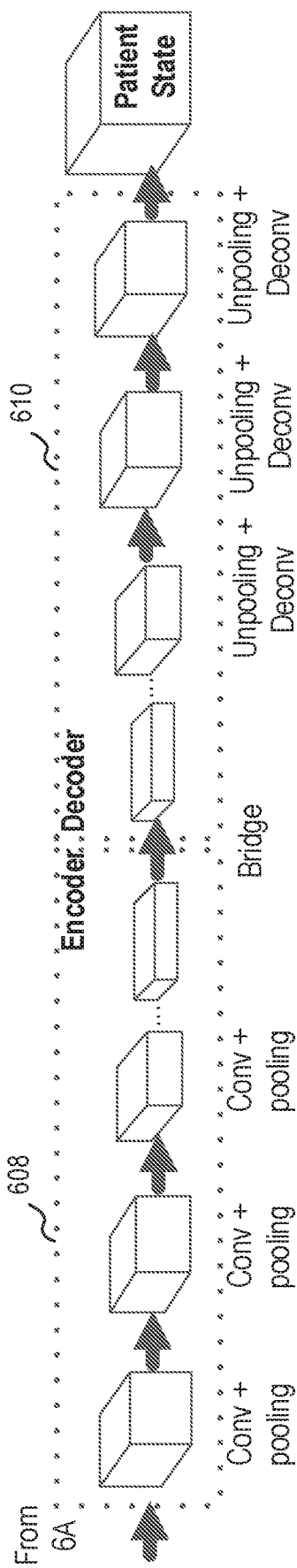

FIGS. 6A-6B illustrate exemplary detailed deep neural network architecture block diagrams. FIG. 6A shows input, convolutional layers, and correlation layers of Network A from the architecture 500 shown in FIG. 5. FIG. 6B shows the patient state generator (encoder-decoder) layers of Network A.

Network A includes a spatio-temporal interpolator the discrete 4D patient model data. Network A is used to generate a new 3D volumetric dataset that best represents a current patient state, given the partial measurement (e.g., 2D image) as input. As previously illustrated in FIG. 5, one example architecture of Network A includes multiple 2D and 3D convolutional neural networks (CNN). Specifically, as shown in FIG. 6A, independent convolutional processing streams are used to extract low-level features from the 2D measurement data (2D CNN processing stream 602) and the 4D patient model (3D+time CNN processing stream 604). Then, a correlation layer 606 matches measurement features with model features (as output from processing stream 602 and 604, respectively). The output of the correlation layer 606 may be sent to the patient state generator (having layers for an encoder 608 and a decoder 610) layers shown in FIG. 6B.

In FIG. 6A, the correlation layer includes a matching process that performs multiplicative patch comparisons between measurement features (output of stream 602) and patient model features (output of stream 604). The correlation layer is similar to a convolution layer except that it convolves data with other data (602 output and 604 output) rather than a filter. This correlation layer correlates features extracted from a 2D image with features extracted from multiple 3D volumes in the input patient model.

In an example, each patch of 2D measurement data may be compared with every possible patch in every 3D volume of the patient model. In other examples, a maximum displacement constraint may be defined, such as a hyperparameter that is organ dependent, or another limiting constraint. In an example, hyperparameters are variables that determine network structure or training rate. Hyperparameters may be set before training. The constraint may be used to significantly reduce the dimensionality of the comparison between the output of the streams 602 and 604, which results in a more computationally tractable determination, while still retaining accuracy.

In FIG. 6B, the encoder-decoder layers 608-610 use the correlation layer 606 output to extract high-level abstract representations for the current patient state, which are then decoded into a dense per-pixel patient state prediction.

An encoder-decoder model may include a neural network, such as a convolutional neural network (CNN) or, in another example a recurrent neural network (RNN). An example CNN is shown in FIG. 6B, illustrating an encoder 608 to encode the correlation layer output into high-level abstract representations, which are then sent to a decoder 610 to produce a dense, per-pixel, patient state description. The Network A output may include the output of the decoder 610, which may include a raw 3D patient state (e.g., a grayscale volume) that interpolates the raw data found in the time-discrete 4D patient model (e.g., the patient model input to stream 604).

In an example, Network B may be generally trained to convolve pairs of images. A smaller database of domain-specific data may then be used for fine-tuning the Network B. For example, a local statistical shape and appearance models may be used to generate realistic, domain-specific ground-truth deformations.

Figure 7A:
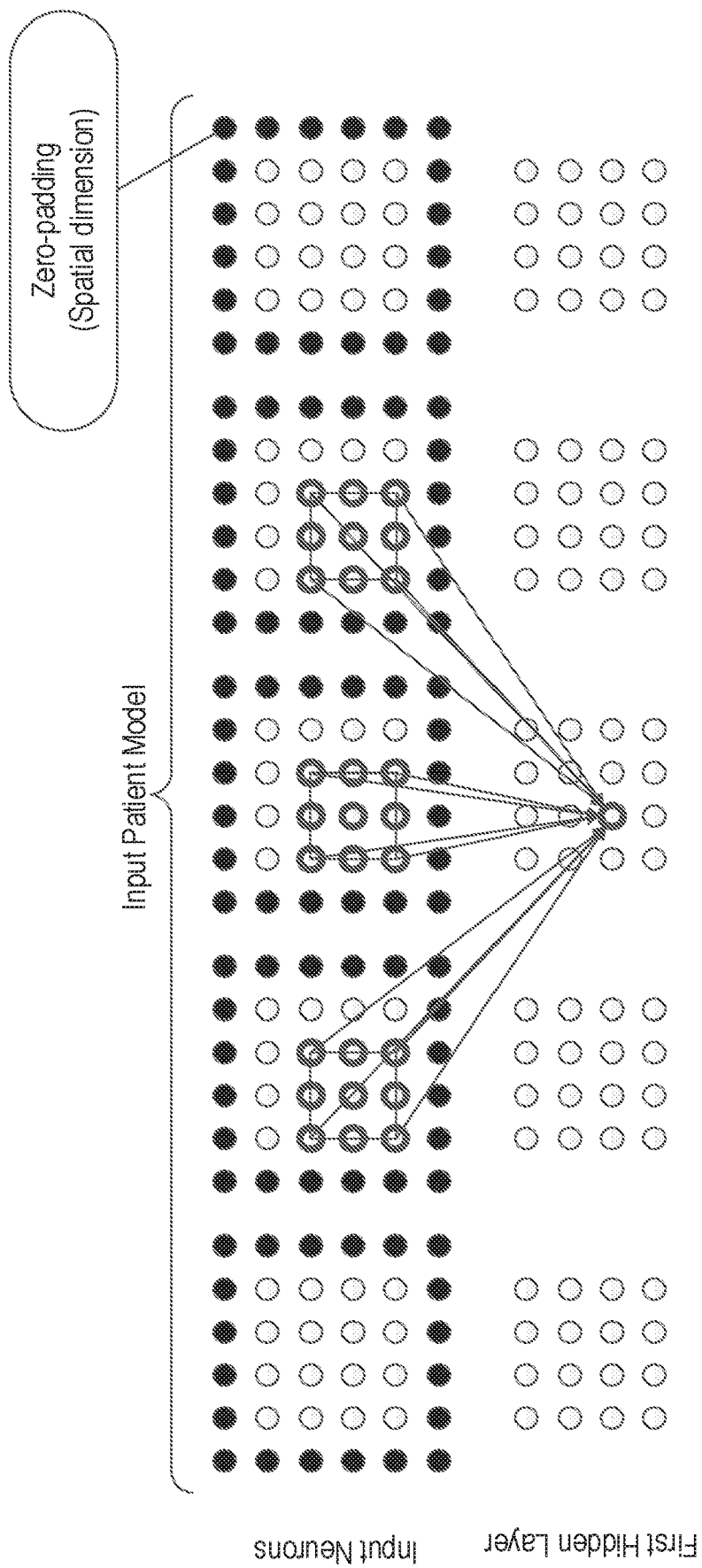
FIGS. 7A-7B illustrate exemplary spatio-temporal convolution diagrams.

Different techniques for encoding and decoding in the CNN may be used. For example, techniques of spatio-temporal convolution for the input patient model are described below in FIGS. 7A-7B, including a zero-padding (7A) and a circular padding (7B) technique. For illustration purposes, only two spatial dimensions are shown, but three dimensional operations may be performed according to similar operations. In an example, zero-padding as shown in FIG. 7A may be used in all spatial dimensions. In another example, circular padding may be used in the time dimension, for example with an assumption that the patient motion is approximately periodic.

Figure 7B:
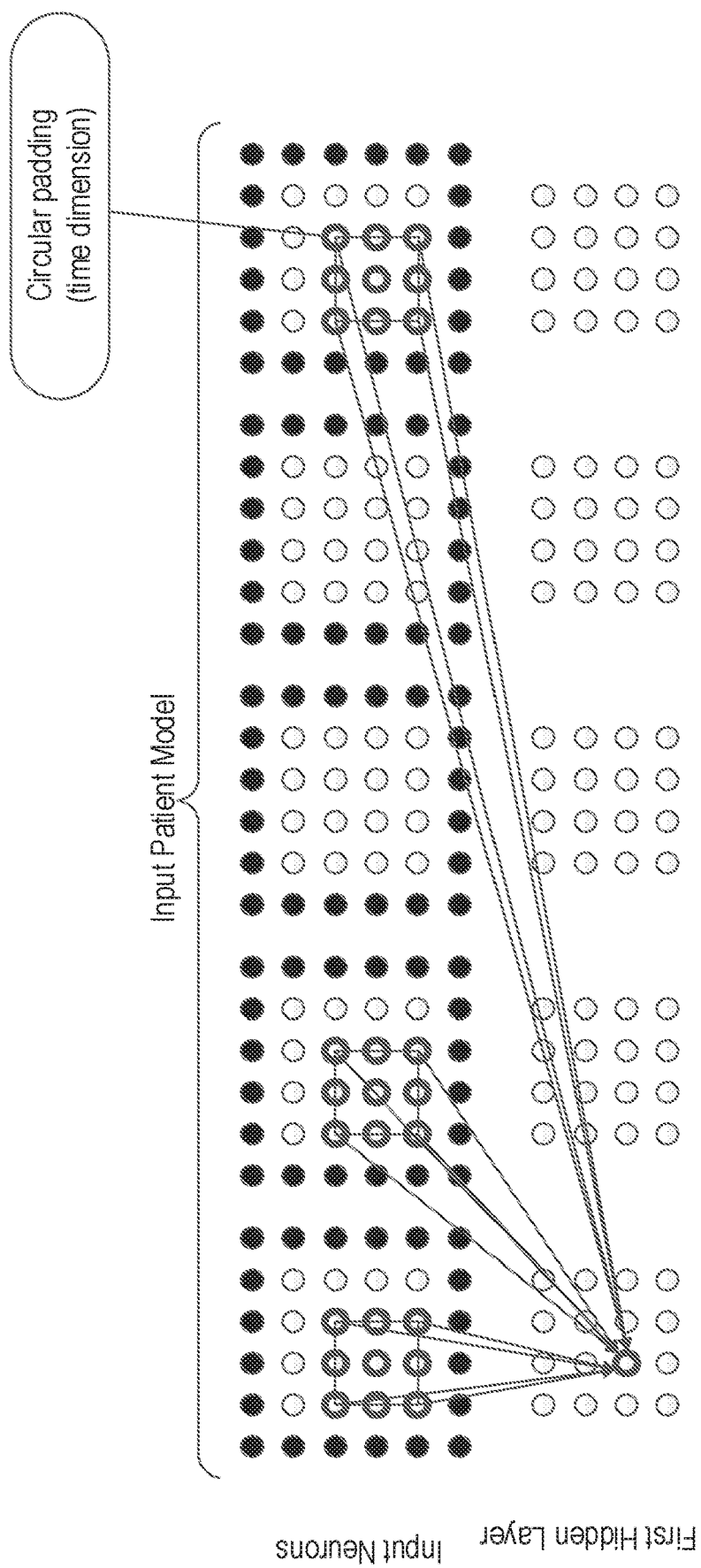

FIGS. 7A-7B illustrate exemplary spatio-temporal convolution diagrams.

FIG. 7A shows a zero-padding approach to a 2D measurement CNN. This CNN processing stream is applied to the 2D measurement using multiple hidden layers that interleave convolutional layers with pooling. The convolutional layers extract multiple abstract spatial features of the image, while the pooling spatially shrinks the feature map. The number of hidden layers and the size of feature space or the number of convolutions at each layer may be hyperparameters that are optimized during training.

FIG. 7B shows a circular padding approach to a 3D and time patient model CNN. In an example, identical 3D CNN processing streams are applied to each volume in the 4D patient model. These streams may not be independent and they may be interconnected with their neighboring processing streams to learn rich spatio-temporal features about an organ's spatial deformation over time. A circular convolution scheme is used, such as under the assumption that the motion described in the 4D patient model is periodic.

Figure 8:
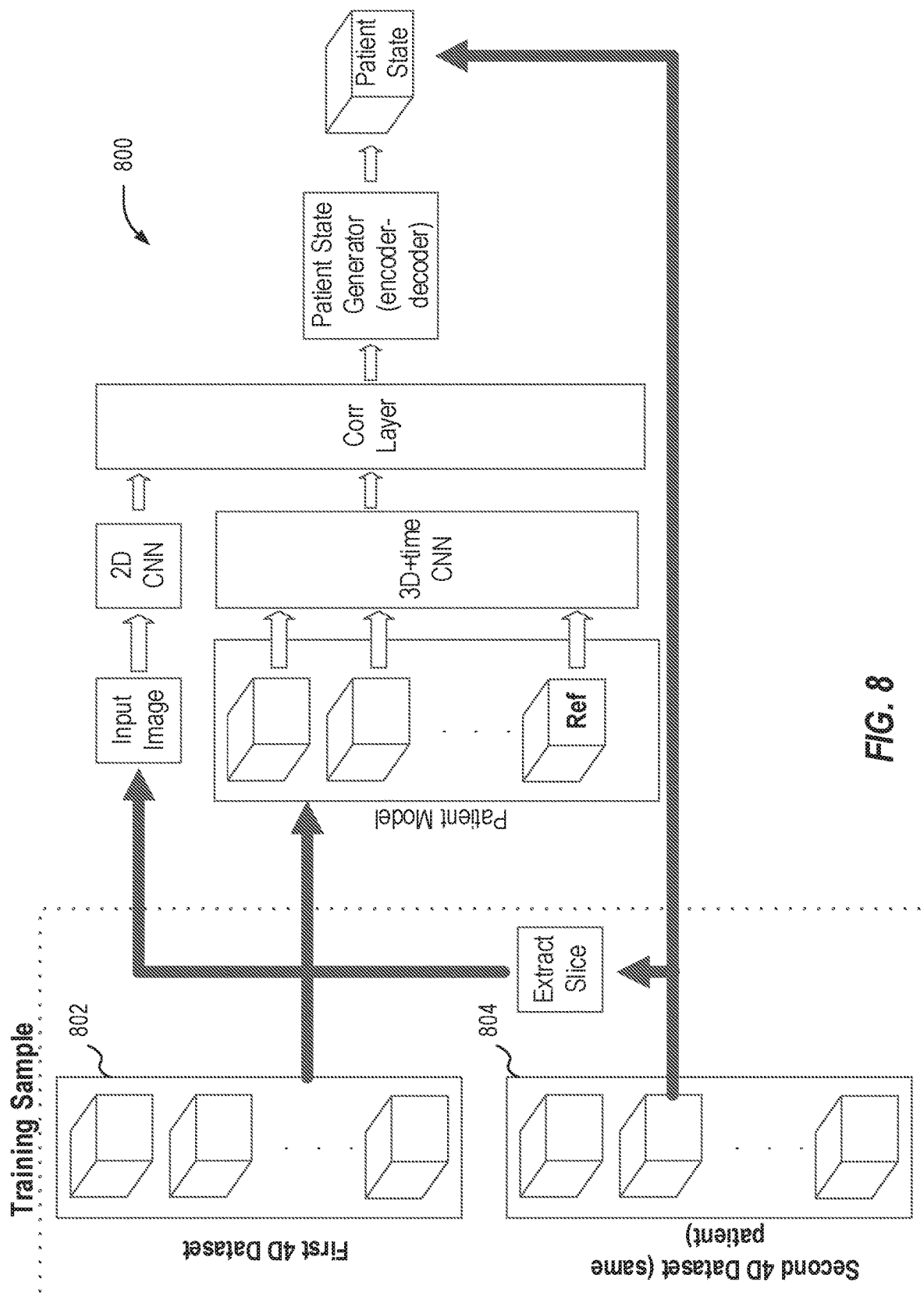
FIG. 8 illustrates an exemplary training flow diagram for a deep neural network.

FIG. 8 illustrates an exemplary training flow diagram 800 for a deep neural network. The diagram 800 includes a training example for Network A (e.g., of FIGS. 5, 6A, 6B, 7A, and 7B). The training is used to generate a patient model interpolator to output a patient state. Network A may be trained using a large database of 4D patient models on which are created synthetic measurement samples and synthetic output patient state samples. In an example, two 4D datasets per patient may be acquired. In some of these examples, two or more 4D datasets for a single patient may be used, in other examples, one or more 4D datasets for two or more patients may be used. As illustrated in FIG. 8, the volume series from a first 4D dataset 802 is used as the input patient model. A volume from the second 4D dataset 804 may be used as the output patient state (e.g., with each volume from the second 4D dataset 805 used sequentially as the output patient state). Realistic 2D measurements may be synthesized from the output patient state. In an example MRI case, a 2D measurement may be synthesized by extracting a 2D slice of data (e.g., averaging multiple slices to best match the slice thickness of a 2D MRI acquisition). In an example CT case, a synthetic 2D x-ray measurement may be generated, for example, using a Siddon-Jacobs ray-tracing algorithm.

In an example, a training sample is created from two 4D datasets acquired on the same patient. The training sample includes a first 4D dataset used as a patient model and a second 4D dataset used as a resulting patient state, as well as an input image from an extracted slice of the second 4D dataset. In an example, the input image may be a 2D measurement slice synthetically created from a volume and used as input. In an example, the two 4D datasets may be permuted to generate more training samples. In another example, samples may be generated from many patients, such as with pairs of datasets from each patient.

Figure 9:
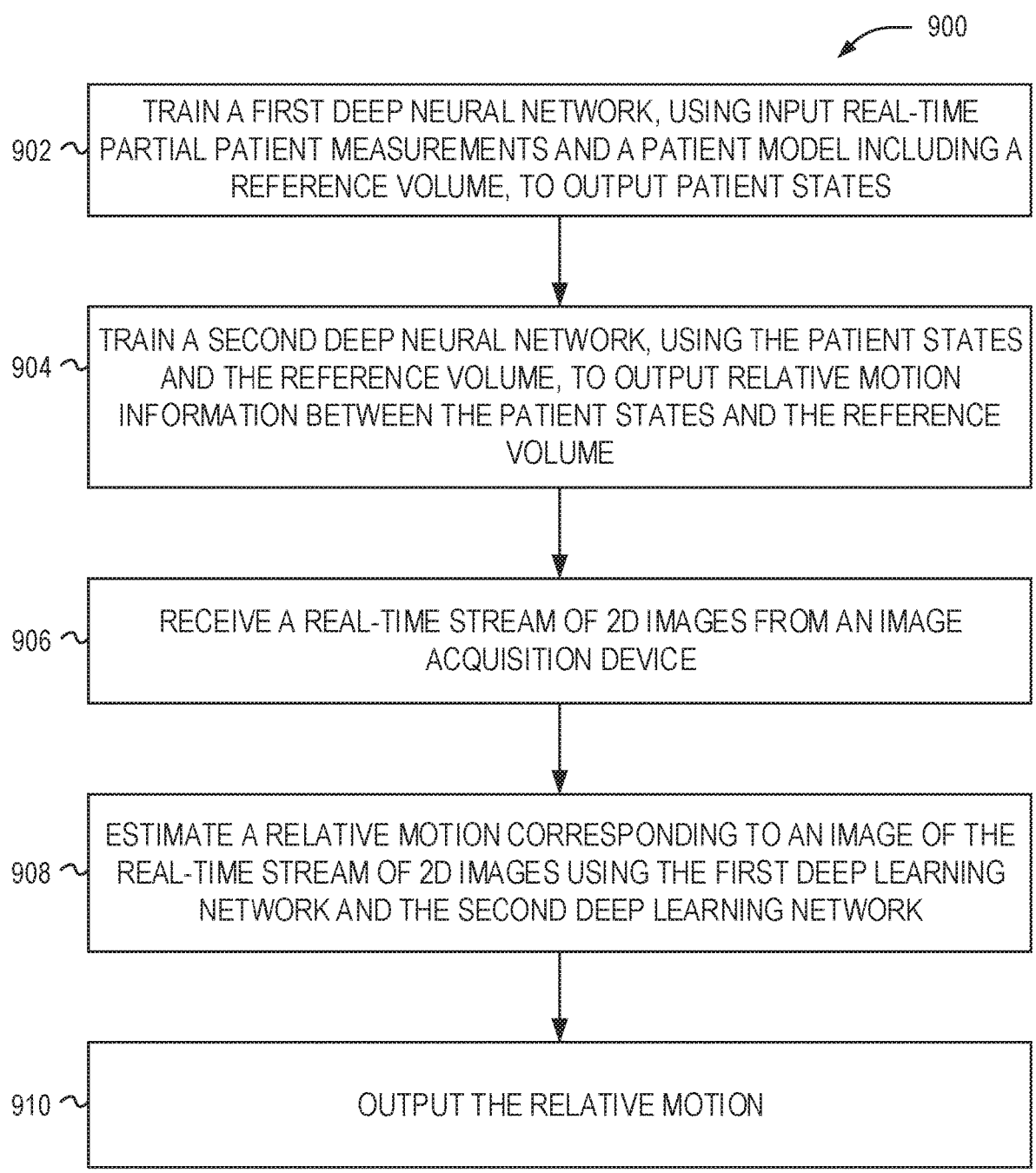
FIG. 9 a flowchart of exemplary operations for estimating relative motion during a radiation therapy procedure.

FIG. 9 illustrates a flowchart of exemplary operations for estimating relative motion during a radiation therapy procedure.

The flowchart 900 includes an operation 902 to train a first deep neural network, using input real-time partial patient measurements and a patient model including a reference volume, to output patient states. In an example, the reference volume may include an MR image synthesized by extracting a 2D slice of data from a 3D or 4D MRI. In another example, the reference volume may include a CT image synthesized by generating a 2D x-ray from a 3D or 4D CT, such as by using a ray-tracing algorithm. In an example, the reference volume is one phase of a 4D patient model. In an example, the reference volume is extracted at an end-of-exhale time in a periodic motion of a patient.

Operation 902 may include using a large database of multi-patient data, and wherein the output patient states are patient-specific due to the patient-specific input real-time partial patient measurements. In an example, operation 902 may include using two 4D datasets. For example a slice may be extracted from a first 4D dataset to use as an input image. In this example, a second 4D dataset may be used as the patient model. The first 4D dataset may be used as an output patient state. In an example, the first deep neural network output is a grayscale volume that interpolates raw data from a time-discrete 4D patient model.

The flowchart 900 includes an operation 904 to train a second deep neural network, using the patient states and the reference volume, to output relative motion information between the patient states and the reference volume.

The flowchart 900 includes an operation 906 to receive a real-time stream of 2D images from an image acquisition device.

The flowchart 900 includes an operation 908 to estimate a relative motion corresponding to an image of the real-time stream of 2D images using the first deep learning network and the second deep learning network. The relative motion may include a 3D displacement vector field (DVF) between a patient state output from the first deep neural network and the reference volume. In an example, the DVF is used to adapt a treatment plan to changes detected between the reference volume, (e.g., the reference volume on which the treatment plan was made), and the patient state.

The flowchart 900 includes an operation 910 to output the relative motion.

The first deep neural network may include a first CNN for the input images, a second CNN for the 4D input, and a correlation layer to match features output from the first CNN and the second CNN. The second CNN may use circular convolution in a time dimension when the relative motion is periodic. In an example, the first CNN may use zero-padding convolution. The patient state generator may include an encoder-decoder CNN model used to encode an output of the correlation layer into a high-level representation and to produce a dense, per-pixel, patient state description. In an example, each patch of the images of the real-time stream of images may be compared with patches in 3D volumes of the patient model. These comparisons may be subject to a maximum displacement constraint (e.g., a hyperparameter), for example one that is dependent on an organ captured within the images.

The relative motion may be used to locate a radiation therapy target within a patient using the patient state.

The flowchart 900 may include an operation to track a radiation therapy target of a patient in real-time using the relative motion. For example, successive images from the real-time stream of images may be used to output corresponding relative motion, with a target tracked from one patient state to the next.

The flowchart 900 may include an operation to direct radiation therapy, using a treatment device (e.g., a stand-alone treatment device, a device coupled to an image acquisition device (e.g., an MR-linac), or the like), to a target according to the relative motion. For example, the target may be located in or tracked, and radiation therapy may be applied according to the location or tracking. In an example, location or tracking information may be displayed on a display device, such as with a user interface presented on the display device.

Additional Notes

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present invention also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and example parameters, functions, and implementations described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Each of these non-limiting examples may stand on its own, or may be combined in various permutations or combinations with one or more of the other examples.

Example 1 is a method comprising: training, using a first deep neural network, a patient state generator to relate input real-time partial patient measurements and a patient model including a reference volume to output patient states; using the patient states output from the first deep neural network and the reference volume as inputs to a second deep neural network to train the second deep learning network to output relative motion information between the patient states and the reference volume; and receiving a real-time stream of images from an image acquisition device; estimating, using the processor, a relative motion corresponding to an image of the real-time stream of images using the first deep learning network and the second deep learning network.

In Example 2, the subject matter of Example 1 includes, wherein the first deep neural network is trained using a large database of multi-patient data, and wherein the output patient states are patient-specific due to the patient-specific input real-time partial patient measurements.

In Example 3, the subject matter of Examples 1-2 includes, wherein the reference volume is an MR image synthesized by extracting a 2D slice of data from an MRI.

In Example 4, the subject matter of Examples 1-3 includes, wherein the reference volume is a CT image synthesized by generating a 2D x-ray using a ray-tracing algorithm.

In Example 5, the subject matter of Examples 1-4 includes, wherein training the first deep neural network includes using two 4D datasets, including extracting a slice from a first 4D dataset to use as an input image, using a second 4D dataset as the patient model, and using the first 4D dataset as an output patient state.

In Example 6, the subject matter of Examples 1-5 includes, wherein the relative motion is a 3D displacement vector field (DVF) between a patient state output from the first deep neural network and the reference volume.

In Example 7, the subject matter of Example 6 includes, wherein the DVF is used to adapt a treatment plan to changes detected between the reference volume, on which the treatment plan was made, and the patient state.

In Example 8, the subject matter of Examples 1-7 includes, wherein the reference volume is one phase of a 4D patient model.

In Example 9, the subject matter of Examples 1-8 includes, wherein the first deep neural network includes a first CNN for the input images, a second CNN for the 4D input, and a correlation layer to match features output from the first CNN and the second CNN.

In Example 10, the subject matter of Example 9 includes, wherein the second CNN uses circular convolution in a time dimension when the relative motion is periodic.

In Example 11, the subject matter of Examples 9-10 includes, wherein the patient state generator includes an encoder-decoder CNN model used to encode an output of the correlation layer into a high-level representation, and to produce a dense, per-pixel, patient state description.

In Example 12, the subject matter of Examples 9-11 includes, wherein each patch of the images of the real-time stream of images is compared with patches in 3D volumes of the patient model subject to a maximum displacement constraint that is dependent on an organ captured within the images.

In Example 13, the subject matter of Examples 1-12 includes, wherein the first deep neural network output is a grayscale volume that interpolates raw data from a time-discrete 4D patient model.

In Example 14, the subject matter of Examples 1-13 includes, wherein the reference volume is extracted at an end-of-exhale time in a periodic motion of a patient.

Example 15 is a method comprising: training, using a processor, a first deep neural network, using input real-time partial patient measurements and a patient model including a reference volume, to output patient states; training a second deep neural network, using the patient states and the reference volume, to output relative motion information between the patient states and the reference volume; and receiving a real-time stream of images from an image acquisition device; estimating, using the processor, a relative motion corresponding to an image of the real-time stream of images using the first deep learning network and the second deep learning network; and outputting the relative motion for display on a display device.

In Example 16, the subject matter of Example 15 includes, using the relative motion to track a radiotherapy target.

In Example 17, the subject matter of Examples 15-16 includes, displaying a location of a radiotherapy target on the display device using the relative motion.

Example 18 is a non-transitory machine-readable medium including instructions, which when executed by a processor, cause the processor to: train a first deep neural network, using input real-time partial patient measurements and a patient model including a reference volume, to output patient states; train a second deep neural network, using the patient states and the reference volume, to output relative motion information between the patient states and the reference volume; and receive a real-time stream of images from an image acquisition device; estimate a relative motion corresponding to an image of the real-time stream of images using the first deep learning network and the second deep learning network; and output the relative motion.

In Example 19, the subject matter of Example 18 includes, wherein the instructions further cause the processor to use the relative motion to track a radiotherapy target.

In Example 20, the subject matter of Examples 18-19 includes, wherein the instructions further cause the processor to display a location of a radiotherapy target on a display device using the relative motion.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method comprising:
    training, using a first deep neural network, a patient state generator to relate input real-time partial patient measurements and a patient model including a reference volume to output patient states;
    using the patient states output from the first deep neural network and the reference volume as inputs to a second deep neural network to train the second deep learning network to output relative motion information between the patient states and the reference volume; and
    receiving a real-time stream of images from an image acquisition device;
    estimating, using a processor, a relative motion corresponding to an image of the real-time stream of images using the first deep learning network and the second deep learning network; and
    outputting the relative motion as a 3D displacement vector field (DVF) between a patient state output from the first deep neural network and the reference volume.

2. The method of claim 1, wherein the first deep neural network is trained using a large database of multi-patient data, and wherein the output patient states are patient-specific due to the patient-specific input real-time partial patient measurements.

3. The method of claim 1, wherein the reference volume is an MR image synthesized by extracting a 2D slice of data from an MRI.

4. The method of claim 1, wherein the reference volume is a CT image synthesized by generating a 2D x-ray using a ray-tracing algorithm.

5. The method of claim 1, wherein training the first deep neural network includes using two 4D datasets, including extracting a slice from a first 4D dataset to use as an input image, using a second 4D dataset as the patient model, and using the first 4D dataset as an output patient state.

6. The method of claim 1, wherein the DVF is used to adapt a treatment plan to changes detected between the reference volume, on which the treatment plan was made, and the patient state.

7. The method of claim 1, wherein the reference volume is one phase of a 4D patient model.

8. The method of claim 1, wherein the first deep neural network includes a first CNN for the input images, a second CNN for the 4D input, and a correlation layer to match features output from the first CNN and the second CNN.

9. The method of claim 8, wherein the second CNN uses circular convolution in a time dimension when the relative motion is periodic.

10. The method of claim 8, wherein the patient state generator includes an encoder-decoder CNN model used to encode an output of the correlation layer into a high-level representation, and to produce a dense, per-pixel, patient state description.

11. The method of claim 8, wherein each patch of the images of the real-time stream of images is compared with patches in 3D volumes of the patient model subject to a maximum displacement constraint that is dependent on an organ captured within the images.

12. The method of claim 1, wherein the first deep neural network output is a grayscale volume that interpolates raw data from a time-discrete 4D patient model.

13. The method of claim 1, wherein the reference volume is extracted at an end-of-exhale time in a periodic motion of a patient.

14. A method comprising:
    training, using a processor, a first deep neural network, using input real-time partial patient measurements and a patient model including a reference volume, to output patient states;
    training a second deep neural network, using the patient states and the reference volume, to output relative motion information between the patient states and the reference volume; and
    receiving a real-time stream of images from an image acquisition device;
    estimating, using the processor, a relative motion corresponding to an image of the real-time stream of images using the first deep learning network and the second deep learning network; and
    outputting the relative motion as a 3D displacement vector field (DVF) between a patient state output from the first deep neural network and the reference volume for display on a display device.

15. The method of claim 14, further comprising using the relative motion to track a radiotherapy target.

16. The method of claim 14, further comprising displaying a location of a radiotherapy target on the display device using the relative motion.

17. A non-transitory machine-readable medium including instructions, which when executed by a processor, cause the processor to:
    train a first deep neural network, using input real-time partial patient measurements and a patient model including a reference volume, to output patient states;
    train a second deep neural network, using the patient states and the reference volume, to output relative motion information between the patient states and the reference volume; and
    receive a real-time stream of images from an image acquisition device;
    estimate a relative motion corresponding to an image of the real-time stream of images using the first deep learning network and the second deep learning network; and
    output the relative motion as a 3D displacement vector field (DVF) between a patient state output from the first deep neural network and the reference volume.

18. The machine-readable medium of claim 17, wherein the instructions further cause the processor to use the relative motion to track a radiotherapy target.

19. The machine-readable medium of claim 17, wherein the instructions further cause the processor to display a location of a radiotherapy target on a display device using the relative motion.

* * * * *